United States Patent [19]
Cashin et al.
[11] 4,027,035
[45] May 31, 1977

[54] THERAPEUTIC USES OF ADAMANTANEALKYLAMINE COMPOUNDS

[75] Inventors: Colin H. Cashin; Jiban K. Chakrabarti, both of Frimley, England; Stephen S. Szinai, Gainsville, Fla.

[73] Assignee: Eli Lilly and Company, London, England

[22] Filed: Aug. 28, 1975

[21] Appl. No.: 608,613

Related U.S. Application Data

[60] Division of Ser. No. 417,174, Nov. 19, 1973, Pat. No. 3,929,888, which is a continuation-in-part of Ser. No. 852,090, Aug. 21, 1969, abandoned.

[30] Foreign Application Priority Data

Aug. 27, 1968 United Kingdom ............ 40968/68

[52] U.S. Cl. .............................................. 424/330
[51] Int. Cl.[2] ........................................ A61K 31/27
[58] Field of Search ............................ 424/330, 316

[56] References Cited

UNITED STATES PATENTS 3,270,036 8/1966 Bernstein et al. ............ 424/330 X

*Primary Examiner*—Albert T. Meyers
*Assistant Examiner*—Daren M. Stephens
*Attorney, Agent, or Firm*—Kathleen R. S. Page; Everet F. Smith

[57] ABSTRACT

2-Phenyl adamantane alkyl amines are useful as antidepressants and anti-Parkinsonism agents, and may be prepared by a Friedel Crafts synthesis involving reaction of benzene with corresponding 2-halogeno compounds.

4 Claims, No Drawings

THERAPEUTIC USES OF ADAMANTANEALKYLAMINE COMPOUNDS

CROSS-REFERENCE TO RELATED APPLICATIONS

This is a division of application Ser. No. 417,174, filed Nov. 19, 1973, and issued Dec. 30, 1975, as U.S. Pat. No. 3,929,888. Application Ser. No. 417,174 was, in turn, a continuation-in-part of application Ser. No. 852,090, filed Aug. 21, 1969, and abandoned after the filing of application Ser. No. 417,174.

BRIEF SUMMARY OF THE INVENTION

The present invention is directed to novel adamantanealkylamine compounds and to therapeutic methods employing and therapeutic compositions comprising adamantanealkylamine compounds. The novel compounds to be employed in these therapeutic methods and compositions are those compounds of the following formula and their pharmaceutically acceptable acid addition salts:

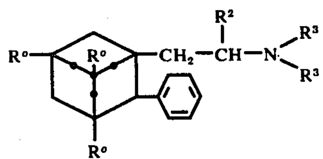

wherein each $R^0$ independently represents hydrogen or methyl; $R^2$ represents hydrogen or alkyl of $C_1$–$C_4$; and each $R^3$ independently represents hydrogen, alkyl of $C_1$–$C_4$, or (2-hydroxyethyl), subject to the limitation that at least one of $R^2$ and $R^3$ is other than hydrogen.

Within the above group of compounds of formula I, a preferred sub-group are those in which each $R^0$ represents hydrogen, and $R^2$ and each $R^3$ independently represent hydrogen, methyl or ethyl.

DETAILED DESCRIPTION OF THE INVENTION

A general synthetic route to the 2-halogenoadamantane intermediates of use in preparing the compounds of formula I has been disclosed in prior copending application Ser. No. 675,037, filed Oct. 13, 1967 and issued July 6, 1971, as 3,591,642. In accordance with that disclosure, 1-adamantanol is reacted with a dialkyl malonate and subsequently hydrolyzed and decarboxylated to produce 1-adamantaneacetic acid. Alternatively, the 1-adamantaneacetic acid can be produced by reaction of the 1-adamantanol with vinylidene chloride. From either source, the 1-adamantaneacetic acid is converted to the acid chloride, which by reaction with an alkoxy magnesium malonate followed by hydrolysis yields the corresponding 1-(1-adamantyl)-2-alkanone:

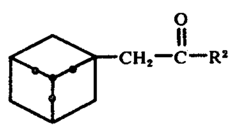

Either this ketone or the 1-adamantaneacetaldehyde is then subjected to reductive amination to obtain the corresponding 1-adamantane-ethylamine. On treatment with sodium hypochlorite or hypobromite, followed by photochemical irridiation, the corresponding 2-chloro or 2-bromo compound is procured.

In like manner are prepared the 2-halogenoadamantane intermediates wherein one or more $R^0$ groups are methyl: the reaction sequence is begun with, instead of 1-adamantanol, a substituted 1-adamantanol.

The resultant 2-halogenoadamantane alkyl amine intermediates are then converted to the 2-phenyl compounds of formula I by a Friedel-Crafts' synthesis involving reaction of benzene in the presence of aluminum chloride or a similar suitable catalyst. Also, compounds wherein both $R^3$ represent alkyl groups can be obtained from the corresponding compounds in which one $R^3$ represents hydrogen, by conventional alkylation procedures. In the instance of all compounds of the present invention, pharmaceutically acceptable acid addition salts are prepared in accordance with known procedures by the reaction of a given compound with the desired acid.

The following examples illustrate the preparation of the compounds of the present invention and will enable those skilled in the art to practice the same.

EXAMPLE 1

2 PHENYL-N,α,DIMETHYL-1-ADAMANTANEETHYLAMINE HYDROCHLORIDE

A solution of 2-chloro-N,α-dimethyl-1-adamantaneethylamine (0.5 g.) in benzene (25 ml.) was added dropwise over one hour to a refluxing solution of anhydrous aluminium chloride (0.83 g.) in benzene (25 ml.), and the mixture was heated at reflux for a further two hours. The reaction mixture was then cooled and poured onto an ice-cold solution of 6N hydrochloric acid (200 ml.) and allowed to stand for 15 minutes. The solution was basified with 10 percent sodium hydroxide solution and the organic phase separated. The aqueous layer was washed once with ether, and then the ether and benzene layers were combined. The combined solutions were washed with several volumes of water until the washings were neutral to litmus, and then dried over anhydrous magnesium sulfate. Removal of solvents by evaporation in vacuo left 522 mg. of an oil. The oil was dissolved in ether, and 2.5 ml. of N hydrochloric acid in ethanol were added. The solution was diluted to 50 ml. with dry ether and after a while white crystals began to separate. The crystals were filtered off, washed with ether and dried in vacuo over phosphorus pentoxide to yield 477 mg. Two hundred milligrams of the crystals were recrystallized from an ethanol ether mixture to yield 178 mg. of pure 2-phenyl-N,α-dimethyl-1-adamantane-ethylamine hydrochloride.

Analysis, Calc : C, 75.08; H, 9.45; N, 4.38; Cl, 11.08. Found: C, 7489; H, 9.45; N, 4.64; Cl, 11.00.

EXAMPLE 2: 2-PHENYL-N,N-α-TRIMETHYL-1-ADAMANTANEETHYLAMINE HYDROCHLORIDE

Formic acid (4.5 ml.) and water (0.5 ml.) were added to the 2-phenyl-N,α-dimethyl-1-adamantaneethylamine (1.0 g.) followed by a 40 percent formaldehyde solution (5 ml.). The mixture was heated on a boiling water bath for seven hours and then allowed to stand overnight. The aqueous solvents were removed in vacuo and the residue treated with dilute hydrochloric acid. Excess acid was removed in vacuo and the oily residue extracted between 3N sodium hydroxide and ether. The organic phase was washed twice with water and dried over magnesium sulfate. The ether was then removed in vacuo to leave 1.1 g. of the base as an oil. The base was dissolved in dry ether, and ethereal hyrochloric acid was added in excess. The resulting precipitate was filtered off and dried in vacuo, and then crystallized from an ethanol-ether mixture to yield 0.3 g. of crystals. Recrystallization from an ethanol-ether mixture yielded 2-phenyl-N,N,α-trimethyl-1-adamantaneethylamine hydrochloride, m.p., 186° -90° C.

EXAMPLE 3:

From 2-chloro-N,α,3,5,7-pentamethyl-1-adamantaneethylamine and benzene in accordance with the procedures of Example 1, 2-phenyl-N,α,3,5,7-pentamethyl-1-adamaneethylamine hydrochloride, m.p., 234° -37° C was prepared.

EXAMPLE 4:

From 2-chloro-N,N-diethyl-α-methyl-1-adamantaneethylamine and benzene in accordance with the procedure of Example 1,2-phenyl-N,N-diethyl-α-methyl-1-adamantaneethylamine salicylate was prepared.

EXAMPLE 5:

By treatment of 2-phenyl-N,α,3,5,7-pentamethyl-1-adamantaneethylamine in accordance with the procedures of Example 2, 2-phenyl-N,N,α,3,5,7-hexamethyl-1-adamantaneethylamine hydrochloride, m.p., 213° -16° C, was prepared.

The compounds of the present invention exhibit antidepressant activity in mammals and hence are valuable agents for the treatment of variously caused depressive states, such as, for example, depression associated with acute and chronic psychoses. The compounds of the present invention are also useful for the relief of Parkinsonism. The usefulness of the present compounds has been demonstrated by art recognised test procedures, in which reserpine hypothermia and reserpine induced catalepsy have been created by medication with reserpine.

As noted above, the compounds of the present invention readily form acid addition salts, and those such salts which are pharmaceutically acceptable are equally useful in implementing the practices of the present invention. Pharmaceutically acceptable acid addition salts include the salts of the compounds with acids such as hydrochloric acid, hydrobromic acid, sulfuric acid, nitric acid, phosphoric acid, methanesulfonic acid, formic acid, maleic acid, acetic acid, propionic acid, butryic acid, tartaric acid, valeric acid, glycolic acid, lactic acid, citric acid, gluconic acid, succinic acid, benzoic acid, salicylic acid, and the like.

The dose of a compound of the present invention or pharmaceutically acceptable acid addition salt thereof is not critical. In general, daily dosages of from about 1 to about 100 or more mg./kg. are suitable. Nor is the form in which the compound or salt is administered critical: the compound or salt thereof can be administered orally or by injection, although the former method is generally preferred.

Oral administration of unmodified compound or salt can be made, but it is generally preferred to administer a formulation comprising the compound or salt in combination with pharmaceutically acceptable adjuvants. Thus, for example, a compound or salt of the present invention can be formulated with substances such as lactose, saccharose, sorbitol, mannitol, potato starch, corn starch, cellulose derivatives, or gelatin, to form tablets, which may be additionally coated, such as with sugar solutions. Soft gelatin capsules can also be formulated with, for example, the foregoing substances as well as other substances known to the art of pharmaceutical formulation. For injection of a compound of the present invention or a pharmaceutically acceptable acid addition salt thereof, the compound or salt is formulated in a physiological saline solution.

The following data illustrate the utility of the compounds of the present invention and will enable those skilled in the art to practice the same.

Test Procedures a. REVERSAL OF RESERPINE INDUCED HYPOTHERMIA IN MICE

Groups of five mice (CFW) weighting 19–21 g. were placed individually in cages (6 inches × 4 inches) and injected with 4 mg./kg. reserpine subcutaneously in a dose volume of 0.2 ml. The reserpine was prepared as an injection solution according to the method of Leyden, Pomerantz and Bouchard ("Journal of the American Pharmaceutical Association (Scientific Edition)", 45, 771-775, 1956), and diluted with distilled water prior to use. Test compounds were administered subcutaneously or orally to groups at 10 and 20 mg./kg. two hours after the reserpine injection and rectal temperatures recorded immediately, from each mouse. Further temperature recordings were taken at 15-minute intervals up to one and one-half hours after drug administration, the temperatures being recorded wih a thermistor (Standard Telephones and Cables, Limited, type F15) or in some experiments, with a thermocouple (Sieres, Type RM6). Usually, two compounds (4 groups) were tested on each experiment and a group of control mice used, which were dosed with saline by the same route.

In order to simplify the recording of results, the "temperature index" assessment described by Winter and Nuss (*Toxicology and Applied Pharmacology* 5:247-56, 1963) has been used. Taking as a base the mean initial temperature for each group, the mean temperature changes from this FIG. at 15, 30, 45, 60, 75 and 90 minutes were summed and termed the "temperature index" (TI). Using this system, mice given reserpine alone gave temperature indices in the range of −8 to −16, while drugs were considered active if the TI was greater than 5 units hyperthermic from the control results. If the control group TI was less than −8, or greater than −16, the experiment was repeated.

The results of the evaluation were as reported in the following table, with + symbolizing a TI of from 5 to 10 units hyperthermic from the control group, and ++ symbolizing a TI of more than 10 units hyperthermic from the control group.

b. REVERSAL OF RESERPINE INDUCED CATALEPSY IN RATS

Rats (female Ulstar) weighing 180 to 200 g. were injected subcutaneously with 15 mg./kg. reserpine made up as an injection solution as described in (a) above. Seventeen hours later, they were tested for catalepsy using the following tests:

1. One hind leg placed on a 3 cm high cork.
2. One hind leg placed on a 9 cm. high cork.
3. Rats placed with their feet on parallel bars
4. Rats placed with their feet on a vertical grid (⅜inch mesh). The rats were considered cataleptic if no movement occurred within about 20 seconds and each rat was given a score of 2 on each test (maximum 8). If a rat moved immediately after being placed on an object but then remained immobile, a score of 1 was given. Only rats showing a high degree of catalepsy (scores of 7 or 8) were selected and split into groups of four. Each group was dosed orally with the test compounds using dose volumes of 1 ml. per rat. The rats were retested for catalepsy at intervals over the following 5½ hours.

The degree of reversal of the catalepsy caused by the test compounds was assesed over the 5½ hour period and the results shown in Table I below, with + indicating some effect, + indicating a significant effect and ++ indicating a marked effect.

Table I

| Compound of Example | Reversal of Reserpine induced hypothermia | | Reversal of Reserpine induced catalepsy | |
|---|---|---|---|---|
| | Dosage in mg./kg. | Results observed | Dosage in mg./kg. | Results observed |
| 1 | 10 s.c. | + | 40 | ++ |
| 2 | 10 s.c. | + | 40 | ± |
| 5 | 10 s.c. | + | N.T.* | |
| 2-phenyl-N-methyl-1-adamantaneethylamine hydrochloride | 20 p.o. | ++ | 40 | ++ |
| 2-phenyl-N,N-dimethyl 1-adamantaneethylamine hydrochloride | 40 p.o. | ++ | 40 | ++ |

*N.T. = Not tested

We claim:

1. The method for treating a warm-blooded mammal in need of treatment to control depression or Parkinsonism, which comprises administering to the mammal a therapeutically effective amount of an active agent, said active agent being a compound selected from the group consisting of (1) those compounds of the following formula and (2) their pharmaceutically acceptable acid addition salts:

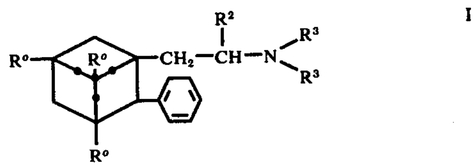

wherein each $R^o$ independently represents hydrogen or methyl; $R^2$ represents hydrogen or alkyl of $C_1$–$C_4$; and each $R^3$ independently represents hydrogen, alkyl of $C_1$–$C_4$, or (2-hydroxy-ethyl), subject to the limitation that at least one of $R^2$ and $R^3$ is other than hydrogen.

2. The method of claim 1 wherein each $R^o$ represents hydrogen and $R^2$ and each $R^3$ independently represents hydrogen, methyl or ethyl.

3. The method of claim 1 wherein the active agent is 2-phenyl-N,N,α-trimethyl-1-adamantaneethylamine hydrochloride.

4. The method of claim 1 wherein the active agent is 2-phenyl-N,α-dimethyl-1-adamantaneethylamine hydrochloride.

* * * * *

UNITED STATES PATENT AND TRADEMARK OFFICE

CERTIFICATE OF CORRECTION

PATENT NO. : 4,027,035

DATED : May 31, 1977

INVENTOR(S) : Colin H. Cashin et al.

It is certified that error appears in the above-identified patent and that said Letters Patent are hereby corrected as shown below:

Title page, left-hand column, item [73], "Eli Lilly and Company" should be -- Lilly Industries Limited --.

Column 2, about line 25, delete the "2"; about line 26, insert -- 2- -- before "PHENYL..."; and about line 56, "7489" should be -- 74.89 --.

Column 3, line 5, "hyro" should be -- hydro --.

Column 4, about line 43, "FIG." should be -- figure --; about line 52, the plus sign should be in quotes; about line 53, the double plus signs should be in quotes; about line 60, "15 mg./kg." should be -- 5 mg./kg. --; and line 68, "The rats...." should be on line 69 at the left margin.

Column 5, line 14, "+" should be -- "$\pm$" --; and line 15, both the plus sign and the double plus sign should be in quotes.

Signed and Sealed this

*First* Day of *November 1977*

[SEAL]

*Attest:*

RUTH C. MASON
*Attesting Officer*

LUTRELLE F. PARKER
*Acting Commissioner of Patents and Trademarks*